United States Patent
Andresen et al.

(12) 
(10) Patent No.: US 10,149,976 B1
(45) Date of Patent: Dec. 11, 2018

(54) PLACEMENT OF NEURAL STIMULATORS

(71) Applicant: Micron Devices LLC, Miami Beach, FL (US)

(72) Inventors: Chad David Andresen, Miami Beach, FL (US); Laura Tyler Perryman, Miami Beach, FL (US)

(73) Assignee: Micron Devices LLC, Pompano Beach, FL (US)

( * ) Notice: Subject to any disclaimer, the term of this patent is extended or adjusted under 35 U.S.C. 154(b) by 54 days.

(21) Appl. No.: 15/062,973

(22) Filed: Mar. 7, 2016

Related U.S. Application Data

(60) Provisional application No. 62/129,534, filed on Mar. 6, 2015.

(51) Int. Cl.
*A61N 1/36* (2006.01)
*A61N 1/05* (2006.01)
*A61N 1/372* (2006.01)

(52) U.S. Cl.
CPC ......... *A61N 1/3605* (2013.01); *A61N 1/0551* (2013.01); *A61N 1/36053* (2013.01); *A61N 1/37205* (2013.01); *A61N 1/36096* (2013.01)

(58) Field of Classification Search
CPC ............ A61N 1/36053; A61N 1/36096; A61N 1/37205; A61N 1/3787; A61N 1/0551; A61N 1/0558; A61N 1/3605
See application file for complete search history.

(56) References Cited

U.S. PATENT DOCUMENTS

2005/0065575 A1* 3/2005 Dobak ............... A61N 1/36007
607/45
2009/0275996 A1* 11/2009 Burnes ................ A61N 1/0558
607/2

FOREIGN PATENT DOCUMENTS

| WO | WO 2012/103519 | 8/2012 |
| WO | WO 2012/138782 | 10/2012 |
| WO | WO 2013/019757 | 2/2013 |
| WO | WO 2013/025632 | 2/2013 |
| WO | WO 2013/040549 | 3/2013 |

* cited by examiner

*Primary Examiner* — Howie Matthews
(74) *Attorney, Agent, or Firm* — Fish & Richardson P.C.

(57) ABSTRACT

A method for implanting a wireless neural stimulator device, the method including: making a surgical incision or a percutaneous opening on a patient's skin; inserting an assembly of an introducer or needle and a needle stylet through the surgical incision or a percutaneous opening and underneath the patient's skin, the needle stylet mounted in an inner lumen of the introducer or needle; withdrawing the needle stylet from the inner lumen of the introducer or needle when the assembly is in place; inserting the wireless neural stimulator device through an inner lumen of the introducer or needle and into the patient's tissue; and withdrawing the introducer from the surgical incision or percutaneous opening.

24 Claims, 16 Drawing Sheets

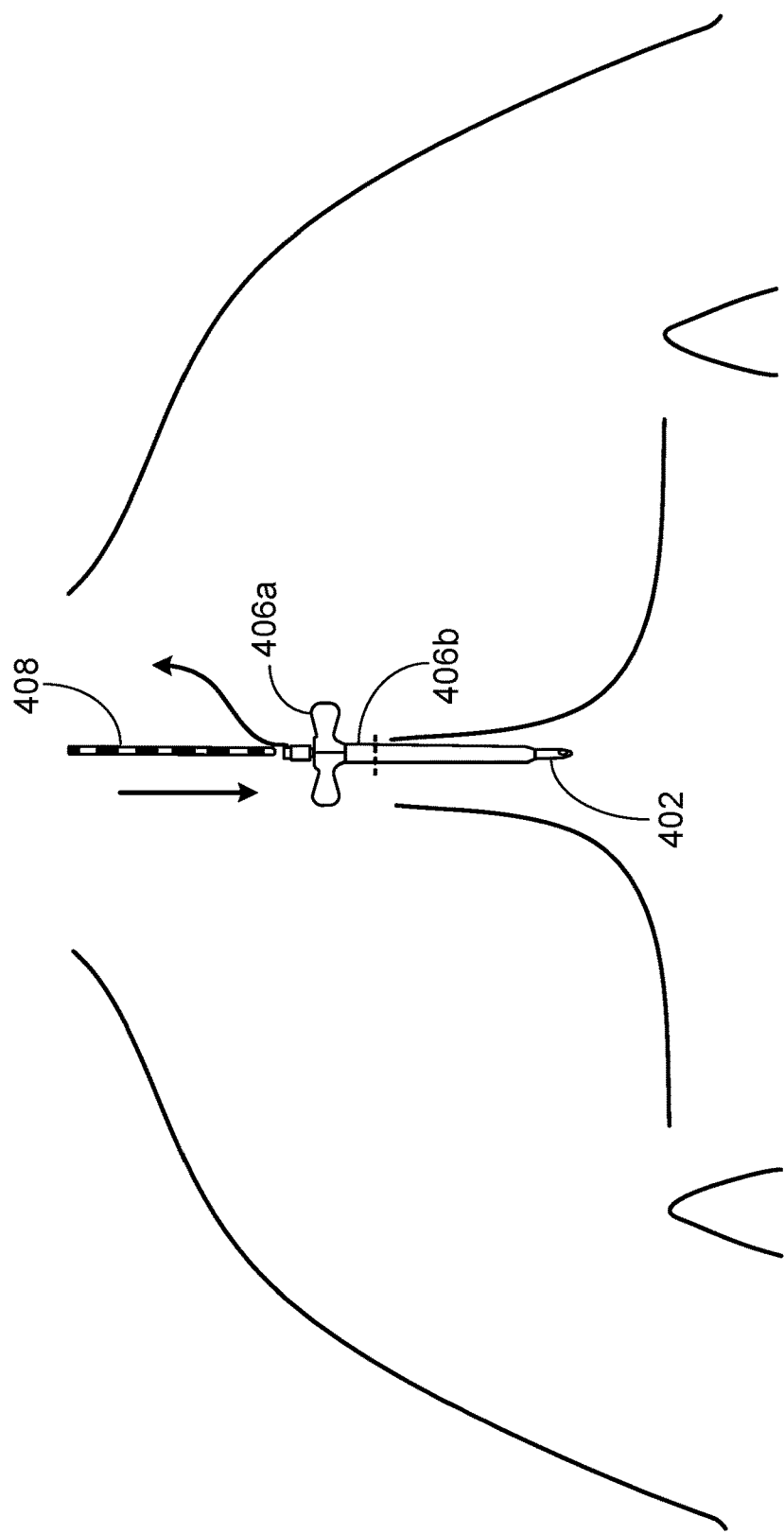

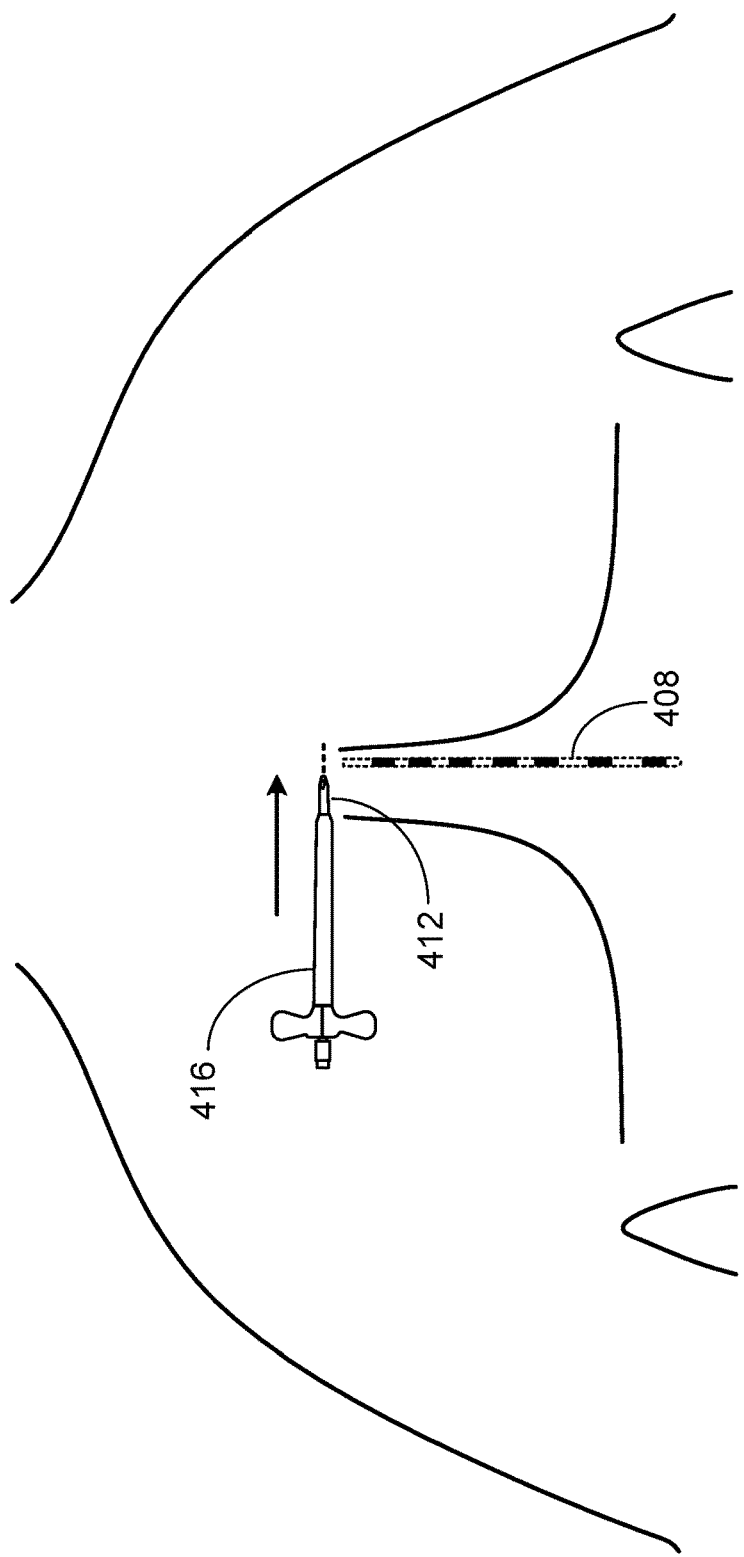

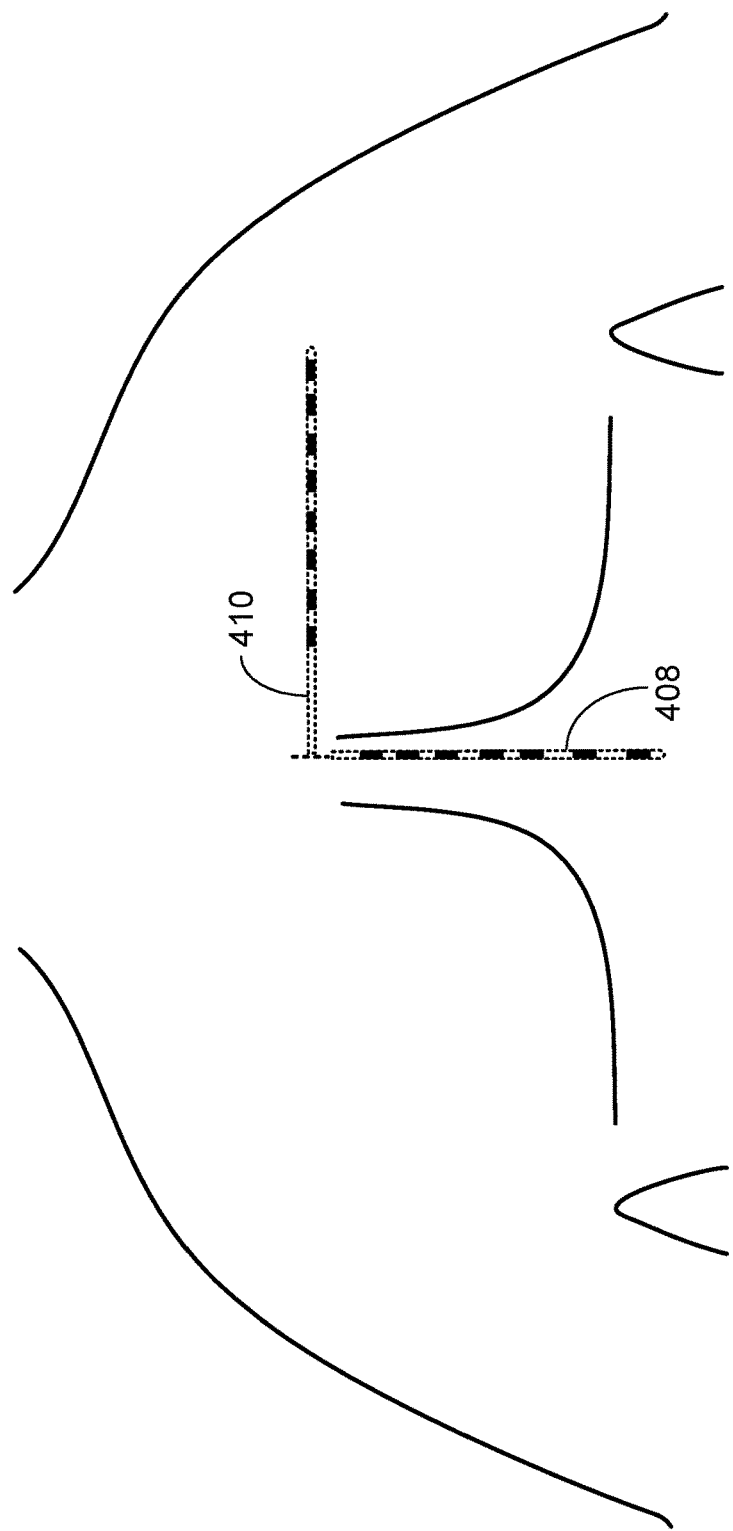

PLACEMENT OF NEURAL STIMULATORS

TECHNICAL FIELD

This application relates generally to procedures for implanting neural stimulators in tissue mediums.

BACKGROUND

Modulation of excitable tissue in the body by electrical stimulation has become an important type of therapy for patients with chronic disabling conditions, including chronic pain, problems of movement initiation and control, involuntary movements, vascular insufficiency, heart arrhythmias and more. A variety of therapeutic intra-body electrical stimulation techniques can treat these conditions. For instance, devices may be used to deliver stimulatory signals to excitable tissue, record vital signs, perform pacing or defibrillation operations, record action potential activity from targeted tissue, control drug release from time-release capsules or drug pump units, or interface with the auditory system to assist with hearing.

SUMMARY

In one aspect, some implementations provide a method for implanting a wireless neural stimulator device. The method includes making a surgical incision or a needle percutaneous opening on a patient's skin; inserting an assembly through an introducer or needle placed through the surgical incision or needle percutaneous opening underneath the patient's skin, the needle stylet mounted in an inner lumen of the introducer or needle; withdrawing the needle stylet from the inner lumen of the introducer or needle when the assembly is in place; inserting the wireless neural stimulator device through an inner lumen of the introducer or needle, and into the patient's tissue at the stimulation site; and withdrawing the introducer or needle from the surgical incision or percutaneous opening.

Implementations may include, but are not limited to, one or more of the following features.

The introducer or needle may be of gauge 13 or smaller. Inserting the assembly of the introducer or needle and the needle stylet may include inserting the assembly of the introducer or needle and the needle stylet under ultrasound guidance. Inserting the assembly of the introducer or needle and the needle stylet may include inserting the assembly of the introducer or needle and the needle stylet under X-ray fluoroscopy, or other imaging technique.

The method may include validating the placement of the wireless neural stimulator device by activating the wireless neural stimulator device using an external microwave field stimulator to induce neural stimulation at the stimulation site. The wireless neural stimulator device may be implanted without implanting an implantable pulse generator (IPG) in the patient's body. The wireless neural stimulator device may be implanted without running a wire to connect the wireless neural stimulator device to an external power source. The surgical incision may be a paramedian incision on an anterior surface of a thoracic cavity of the patient; and wherein the method may include: after inserting the assembly of the introducer or needle and the needle stylet through the surgical incision or percutaneous opening, advancing the assembly laterally until the distal mouth of the introducer or needle is medial of the stimulation site.

The surgical incision or percutaneous opening may be a transverse incision on an anterior surface of a thoracic cavity of the patient; and wherein the method may include: after inserting the assembly of the introducer or needle and the needle stylet through the surgical incision or percutaneous opening, advancing the assembly inferiorly until the distal mouth of the introducer or needle is anterior of the stimulation site.

The surgical incision or percutaneous opening may be made above an ear of the patient. The method may include: after inserting the assembly of the introducer or needle and the needle stylet through the surgical incision or percutaneous opening, advancing the wireless neural stimulator device to a level above the occipital crest; subsequently causing the wireless neural stimulator device to turn and enter into the posterior cranium space of the patient. The method may include: after inserting the assembly of the introducer or needle and the needle stylet through the surgical incision or percutaneous opening, advancing the wireless neural stimulator device into the anterior cranium above the eyebrows space of the patient.

The method may include: anchoring the wireless neural stimulator device to surrounding tissue at the stimulation site. Anchoring the wireless neural stimulator device may include: running a suture to tie the wireless neural stimulator device to surrounding tissue. The wireless neural stimulator device may be implanted such that a distal end of the wireless neural stimulator device is 25 cm or less from the surgical incision or percutaneous opening on the patient's skin. More than one wireless neural stimulator device may be implanted through one surgical incision or percutaneous opening.

The details of one or more implementations are set forth in the accompanying drawings and the description below. Other features, objects, and advantages will be apparent from the description and drawings, and from the claims.

BRIEF DESCRIPTION OF THE DRAWINGS

FIGS. 4A-4G illustrate an example of anterior implantation of wireless neural stimulator device around the thoracic cavity.

Like reference symbols in the various drawings indicate like elements.

DETAILED DESCRIPTION

Figure 1:
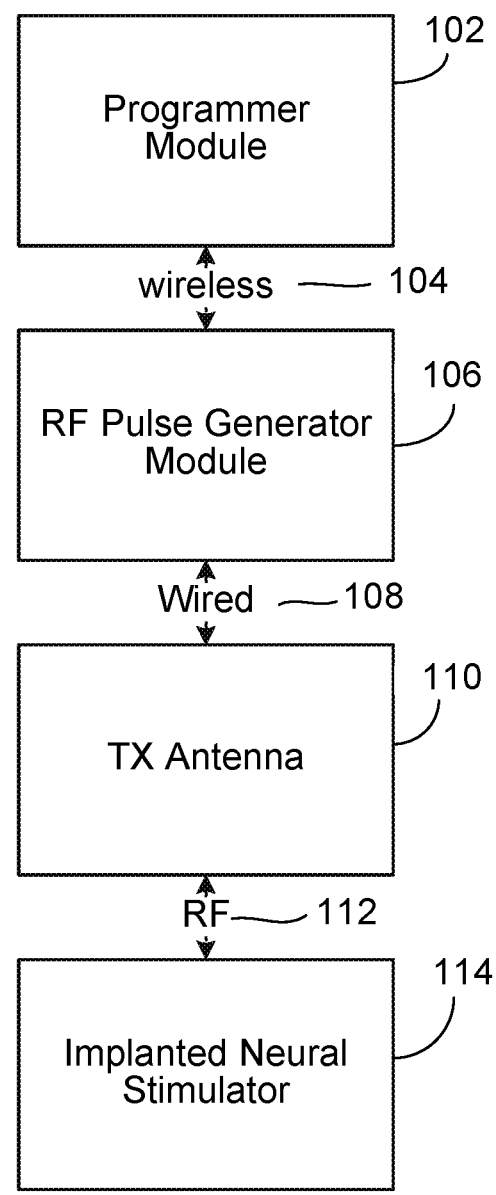
FIG. 1 depicts a high-level diagram of an example of a wireless neural stimulation system.

In various implementations, systems and methods are disclosed for applying one or more electrical impulses to targeted excitable tissue, such as nerves, for treating chronic pain, inflammation, arthritis, sleep apnea, seizures, incontinence, pain associated with cancer, incontinence, problems of movement initiation and control, involuntary movements, vascular insufficiency, heart arrhythmias, obesity, diabetes, craniofacial pain, such as migraines or cluster headaches, and other disorders. In certain embodiments, a device may be used to send electrical energy to targeted nerve tissue by using remote radio frequency (RF) energy without cables or inductive coupling to power a passive implanted wireless neural stimulator device. The targeted nerves can include, but are not limited to, the spinal cord and surrounding areas, including the dorsal horn, dorsal root ganglion, the exiting nerve roots, nerve bundles, the dorsal column fibers and the peripheral nerve bundles leaving the dorsal column and brain, such as the vagus, occipital, trigeminal, hypoglossal, sacral, coccygeal nerves and the like.

A wireless stimulation system can include an implantable wireless neural stimulator device with one or more electrodes and one or more conductive antennas (for example, dipole or patch antennas), and internal circuitry for frequency waveform and electrical energy rectification. The system may further comprise an external controller and antenna for transmitting radio frequency or microwave energy from an external source to the implantable wireless neural stimulator device with neither cables nor inductive coupling to provide power.

In various implementations, the implantable wireless neural stimulator device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling. This allows such devices to produce electrical currents capable of stimulating nerve bundles without a physical connection to an implantable pulse generator (IPG) or use of an inductive coil.

The implantable wireless neural stimulator device disclosed herein may be implanted in a subcutaneous manner to treat angina pain, craniofacial pain, or occipital pain. Subcutaneous implantation can be advantageous in that it creates small surgical incision or percutaneous opening points, only involves local anesthesia, and maintains anti-platelet therapy that the patient may be undergoing. More details of the subcutaneous implantation can be found in FIGS. 3-5 and the discussions thereof.

Further descriptions of exemplary wireless systems for providing neural stimulation to a patient can be found in commonly-assigned, co-pending published PCT applications PCT/US2012/23029 filed Jan. 28, 2011, PCT/US2012/32200 filed Apr. 11, 2011, PCT/US2012/48903, filed Jan. 28, 2011, PCT/US2012/50633, filed Aug. 12, 2011 and PCT/US2012/55746, filed Sep. 15, 2011, the complete disclosures of which are incorporated by reference.

FIG. 1 depicts a high-level diagram of an example of a wireless neural stimulation system. The wireless neural stimulation system may include four major components, namely, a programmer module 102, a RF pulse generator module 106, a transmit (TX) antenna 110 (for example, a patch antenna, slot antenna, or a dipole antenna), and an implanted wireless neural stimulator device 114. The programmer module 102 may be a computer device, such as a smart phone, running a software application that supports a wireless connection 104, such as Bluetooth®. The application can enable the user to view the system status and diagnostics, change various parameters, increase/decrease the desired stimulus amplitude of the electrode pulses, and adjust feedback sensitivity of the RF pulse generator module 106, among other functions.

The RF pulse generator module 106 may include communication electronics that support the wireless connection 104, the stimulation circuitry, and the battery to power the generator electronics. In some implementations, the RF pulse generator module 106 includes the TX antenna embedded into its packaging form factor while, in other implementations, the TX antenna is connected to the RF pulse generator module 106 through a wired connection 108 or a wireless connection (not shown). The TX antenna 110 may be coupled directly to tissue to create an electric field that powers the implanted wireless neural stimulator device 114. The TX antenna 110 communicates with the implanted wireless neural stimulator device 114 through an RF interface. For instance, the TX antenna 110 radiates an RF transmission signal that is modulated and encoded by the RF pulse generator module 110. The implanted wireless neural stimulator device of module 114 contains one or more antennas, such as dipole antenna(s), to receive and transmit through RF interface 112. In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electrical radiative coupling, the TX antenna 110 can provide an input signal to the implanted wireless neural stimulator device 114. This input signal contains energy and may contain information encoding stimulus waveforms to be applied at the electrodes of the implanted wireless neural stimulator device 114. In some implementations, the power level of this input signal directly determines an applied amplitude (for example, power, current, or voltage) of the one or more electrical pulses created using the electrical energy contained in the input signal. Within the implanted wireless neural stimulator device 114 are components for demodulating the RF transmission signal, and electrodes to deliver the stimulation to surrounding neuronal tissue.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulator device 114. In either event, receiver circuit(s) internal to the wireless stimulator device 114 (or cylindrical wireless neural implantable stimulator device 1400 shown in FIGS. 3A and 3B or a helical implantable wireless neural stimulator device) can capture the energy radiated by the TX antenna 110 and convert this energy to an electrical waveform. The receiver circuit(s) may further modify the waveform to create an electrical pulse suitable for the stimulation of neural tissue.

In some implementations, the RF pulse generator module 106 can remotely control the stimulus parameters (that is, the parameters of the electrical pulses applied to the neural tissue) and monitor feedback from the wireless neural stimulator device 114 based on RF signals received from the implanted wireless neural stimulator device 114. A feedback detection algorithm implemented by the RF pulse generator module 106 can monitor data sent wirelessly from the implanted wireless neural stimulator device 114, including information about the energy that the implanted wireless neural stimulator device 114 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless neural stimulator device 114 are monitored and used to determine the appropriate level of neural stimulation current for maintaining effective neuronal activation, or, in some cases, the patient can manually adjust the output signals in an open loop control method.

Figure 2:
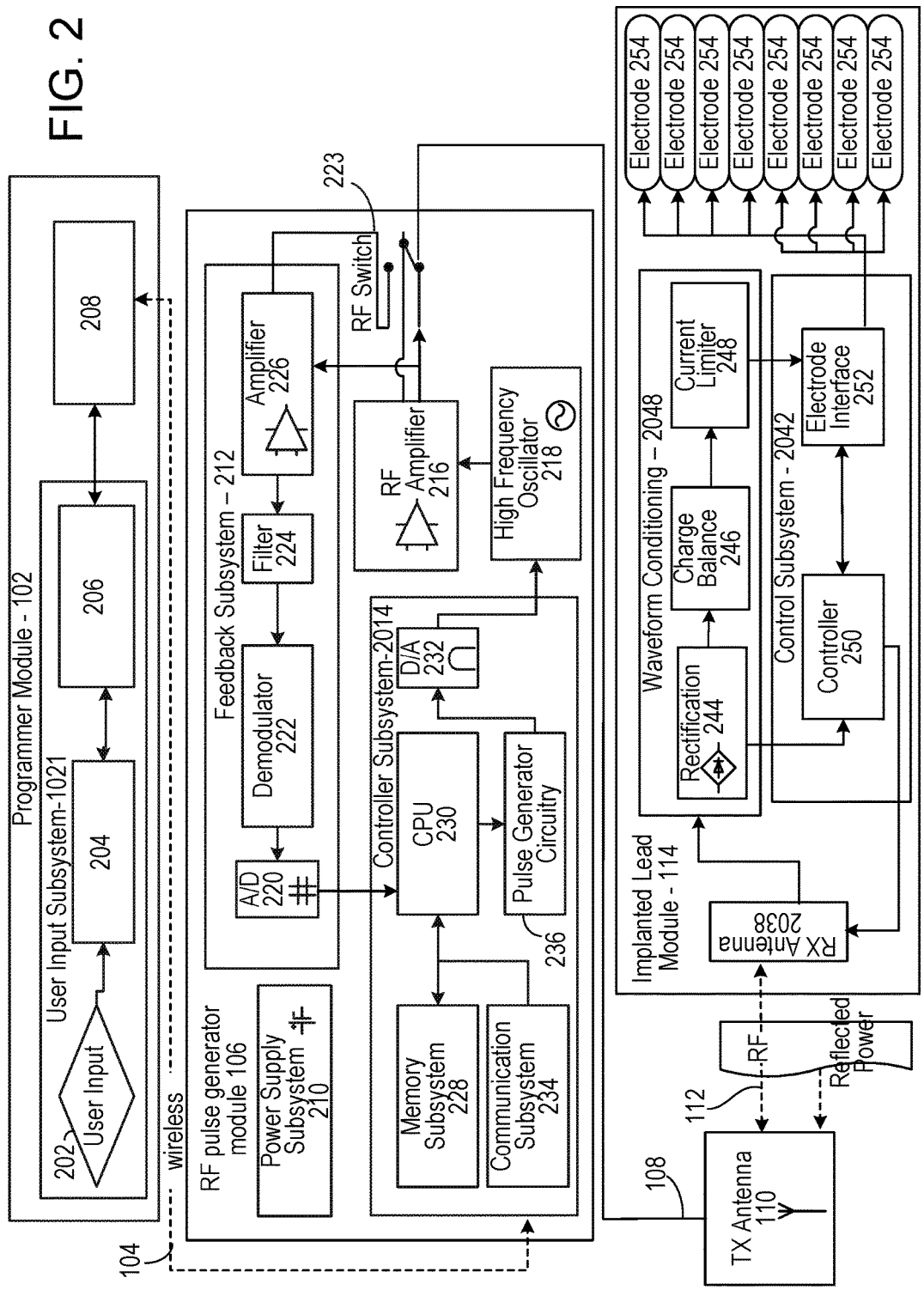
FIG. 2 depicts a detailed diagram of an example of the wireless neural stimulation system.

FIG. 2 depicts a detailed diagram of an example of the wireless neural stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send stimulation parameters to the RF pulse generator module 106. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

| Stimulation Parameter Table 1 | |
| --- | --- |
| Pulse Amplitude: | 0 to 20 mA |
| Pulse Frequency: | 0 to 20000 Hz |
| Pulse Width: | 0 to 2 ms |

The RF pulse generator module 106 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 102 may be functionally a smart device and associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted wireless neural stimulator device 114 may include both power and parameter-setting attributes in regards to stimulus waveform, amplitude, pulse width, and frequency. The RF pulse generator module 106 can also function as a wireless receiving unit that receives feedback signals from the implanted wireless stimulator device 114. To that end, the RF pulse generator module 106 may contain microelectronics or other circuitry to handle the generation of the signals transmitted to the device 114 as well as handle feedback signals, such as those from the stimulator device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 106 to the wireless neural stimulator device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receiving (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 214 may store received parameter settings in the local memory subsystem 228, until the parameter settings are modified by new input data received from the programming module 102. The CPU 206 may use the parameters stored in the local memory to control the pulse generator circuitry 236 to generate a stimulus waveform that is modulated by a high frequency oscillator 218 in the range from 300 MHz to 8 GHz (preferably between about 700 MHz and 5.8 GHz and more preferably between about 800 MHz and 1.3 GHz). The resulting RF signal may then be amplified by RF amplifier 226 and then sent through an RF switch 223 to the TX antenna 110 to reach through depths of tissue to the RX antenna 238.

In some implementations, the RF signal sent by TX antenna 110 may simply be a power transmission signal used by the wireless stimulation device module 114 to generate electric pulses. In other implementations, a telemetry signal may also be transmitted to the wireless neural stimulator device 114 to send instructions about the various operations of the wireless neural stimulator device 114. The telemetry signal may be sent by the modulation of the carrier signal (through the skin if external, or through other body tissues if the pulse generator module 106 is implanted subcutaneously). The telemetry signal is used to modulate the carrier signal (a high frequency signal) that is coupled onto the implanted antenna(s) 238 and does not interfere with the input received on the same stimulator device to power the device. In one embodiment the telemetry signal and powering signal are combined into one signal, where the RF telemetry signal is used to modulate the RF powering signal, and thus the wireless stimulation device is powered directly by the received telemetry signal; separate subsystems in the wireless stimulation device harness the power contained in the signal and interpret the data content of the signal.

The RF switch 223 may be a multipurpose device such as a dual directional coupler, which passes the relatively high amplitude, extremely short duration RF pulse to the TX antenna 110 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110.

During the on-cycle time (when an RF signal is being transmitted to wireless neural stimulator device 114), the RF switch 223 is set to send the forward power signal to feedback subsystem. During the off-cycle time (when an RF signal is not being transmitted to the wireless neural stimulator device 114), the RF switch 223 can change to a receiving mode in which the reflected RF energy and/or RF signals from the wireless neural stimulator device 114 are received to be analyzed in the feedback subsystem 212.

The feedback subsystem 212 of the RF pulse generator module 106 may include reception circuitry to receive and extract telemetry or other feedback signals from the wireless neural stimulator device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can result in unwanted heating of internal components, and this fault condition means the system cannot deliver sufficient power to the implanted wireless stimulation device and thus cannot deliver therapy to the user.

The controller 242 of the wireless neural stimulator device 114 may transmit informational signals, such as a telemetry signal, through the antenna 238 to communicate with the RF pulse generator module 106 during its receive cycle. For example, the telemetry signal from the wireless neural stimulator device 114 may be coupled to the modulated signal on the dipole antenna(s) 238, during the on and off state of the transistor circuit to enable or disable a waveform that produces the corresponding RF bursts necessary to transmit to the external (or remotely implanted) pulse generator module 106. The antenna(s) 238 may be connected to electrodes 254 in contact with tissue to provide a return path for the transmitted signal. An A/D (not shown) converter can be used to transfer stored data to a serialized pattern that can be transmitted on the pulse-modulated signal from the internal antenna(s) 238 of the wireless neural stimulator device 114.

A telemetry signal from the implanted wireless neural stimulator device 114 may include stimulus parameters such as the power or the amplitude of the current that is delivered to the tissue from the electrodes. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulator device 114, and sent on the telemetry signal. The frequency of the carrier signal may be in the range of at 300 MHz to 8 GHz (preferably between about 700 MHz and 5.8 GHz and more preferably between about 800 MHz and 1.3 GHz).

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the wireless neural stimulator device 114 delivered the specified stimuli to tissue. For example, if the wireless neural stimulator device reports a lower current than was specified, the power level from the RF pulse generator module 106 can be increased so that the implanted wireless neural stimulator device 114 will have more available power for stimulation. The implanted wireless neural stimulator device 114 can generate telemetry data in real time, for example, at a rate of 8 Kbits per second. All feedback data received from the implanted wireless neural stimulator device 114 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable wireless neural stimulator device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform conditioning circuitry 240, within the implanted wireless neural stimulator device 114 to be converted into electrical pulses applied to the electrodes 254 through electrode interface 252. In some implementations, the implanted wireless stimulator device 114 contains between two to sixteen electrodes 254.

The waveform conditioning circuitry 240 may include a rectifier 244, which rectifies the signal received by the RX antenna 238. The rectified signal may be fed to the controller 242 for receiving encoded instructions from the RF pulse generator module 106. The rectifier signal may also be fed to a charge balance component 246 that is configured to create one or more electrical pulses based such that the one or more electrical pulses result in a substantially zero net charge at the one or more electrodes (that is, the pulses are charge balanced). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless neural stimulator device 114 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 106. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 106 can reduce the RF power delivered to the body if the implanted wireless neural stimulator device 114 reports it is receiving excess RF power.

The controller 250 of the wireless neural stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless neural stimulator 106 has multiple electrodes 254 in contact with tissue, and for a given stimulus the RF pulse generator module 106 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 106) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 250 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the wireless neural stimulator device 114 may include a charge-balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 $uC/cm^2$. Biphasic stimulating current pulses ensure that no net charge appears at the electrode after each stimulation cycle and the electrochemical processes are balanced to prevent net dc currents. The wireless neural stimulator device 114 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the wireless neural stimulator circuitry and the point of stimulus delivery to tissue. In this manner, a resistor-capacitor (RC) network may be formed. In a multi-electrode wireless neural stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment as disclosed herein, the wireless neural stimulator may have a charge-balance capacitor with a value chosen according to the measured series resistance of the electrodes and the tissue environment in which the wireless neural stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless neural stimulator device 114 may create a drive-waveform envelope that follows the envelope of the RF pulse received by the receiving dipole antenna(s) 238. In this case, the RF pulse generator module 106 can directly control the envelope of the drive waveform within the wireless neural stimulator device 114, and thus no energy storage may be required inside the wireless neural stimulator itself. In this implementation, the wireless neural stimulator circuitry may modify the envelope of the drive waveform or may pass it directly to the charge-balance capacitor and/or electrode-selection stage.

In some implementations, the implanted wireless neural stimulator device 114 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the wireless neural stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless neural stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 106, and in others this control may be administered internally by circuitry onboard the wireless neural stimulator device 114, such as controller 250. In the case of onboard control, the amplitude and timing may be specified or modified by data commands delivered from the pulse generator module 106.

Some methods include implantation of a wireless neural stimulator device to treat conditions such as angina pain or craniofacial pain or occipital pain. Electrodes in some embodiments, may be positioned near targeted nerves in very specific regions, such as the parasternal regions on the chest, where patients usually experience angina. These methods include placement of devices under ultrasound guidance and may be performed as part of an outpatient procedure and may only use local anesthesia. The implanted wireless neural stimulator device does not include a power supply, such as a battery, and is powered remotely by, for example, electromagnetic energy radiated from a microwave field stimulator (MFS). The absence of an independent power source on the implanted wireless stimulator may enable a compact form factor, which is highly conducive to subcutaneous implantation. As such, the implantation method does not include implanting an implantable pulse generator (IPG). Nor does the implantation method including embedding wires that connects the stimulator device to an external power source. Compared to implantation in the epidural space for spinal cord stimulation, implantation at the targeted peripheral nerves does not require special training of the physician. Moreover, such peripheral nerve implantations may not preclude anti-platelet therapy and anticoagulants, something typically administered to patients with angina pain. Generally, placement of the wireless neural stimulator device is less invasive than, for example, implantation in the epidural space of the spinal cord. As such, peripheral nerve placement carries less risk of serious complications, as positioning and securing of electrodes easier compared with epidural placement. Below, examples of peripheral implantation are described in the context of treating angina, craniofacial pain, and occipital pain.

Figure 3A:
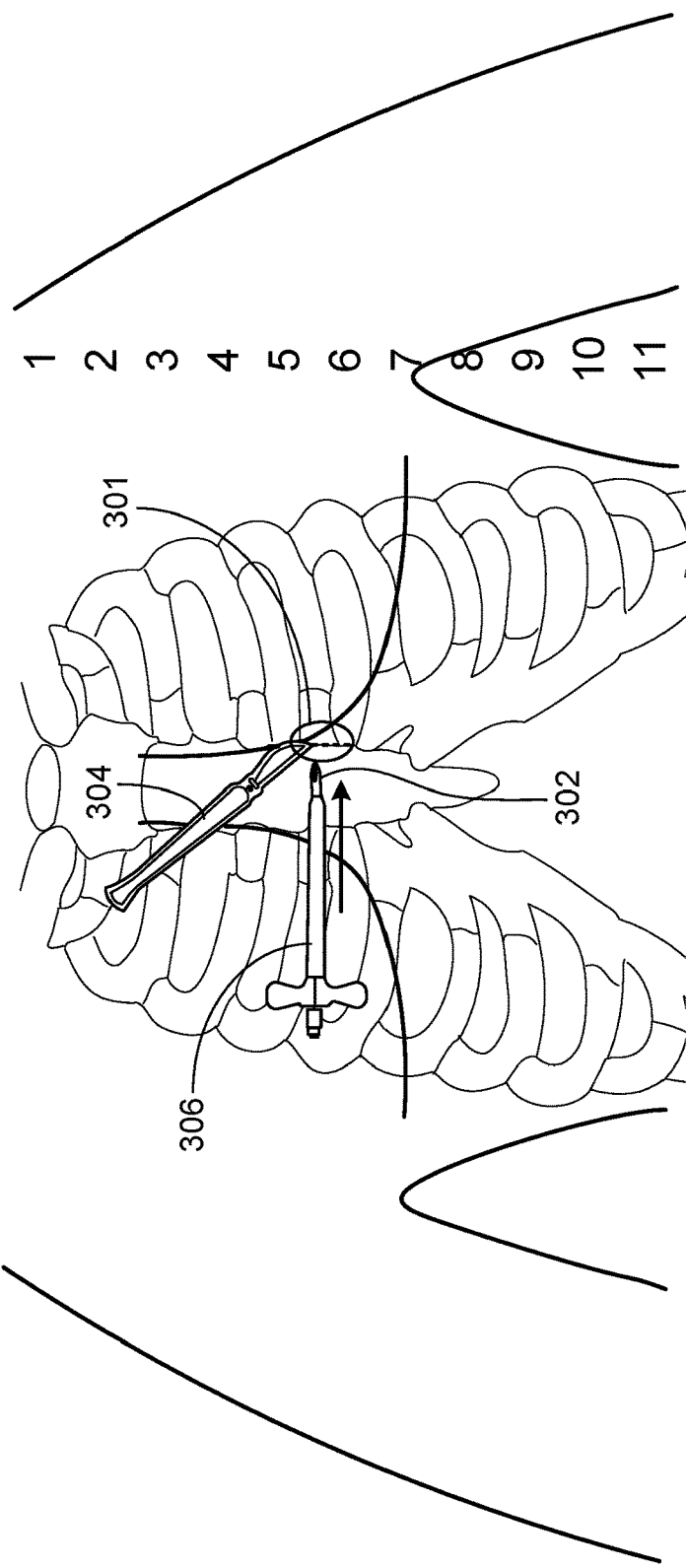
FIGS. 3A-3E illustrate an example of implanting a wireless neural stimulator device to treat angina pain.

FIGS. 3A-3E illustrate an example of implanting a wireless neural stimulator device 308 to treat angina pain. As illustrated in FIG. 3A, initially, a treating physician makes a small surgical incision 301, less than 2 mm long, on the anterior surface of the patient's thoracic cavity, for example, on the left chest of the patient between the third and sixth rib. Entry to the tissue can also be accomplished by a needle entry to create a percutaneous opening, with a 13 gauge or smaller needle. The incision point or percutaneous opening is generally on the skin and over the parasternal space, for example, in the intercostal space. The incision or percutaneous opening may be a paramedian incision or entry, that is, a vertical incision generally parallel and adjacent to the midline. In one example, surgical incision 301 may be made by cutting the skin using scalpel 304 and under local anesthesia. The use of local anesthesia may facilitate patient recovery and reduce procedural complications. In fact, a general physician without specialized training may perform the incision for such implantation. Next, an introducer or needle, 306, along with a needle stylet 302, are inserted through surgical incision 301 or percutaneous opening underneath the patient's skin. Introducer 306 has an elongated, generally tubular sheath section 306a and a handle section 306b. The sheath section 306a may be of gauge 13 or smaller and includes a pair of weakened sections (not illustrated) that extend longitudinally along the sheath 306a and are located opposite one another on the sheath 306a. The handle section 306b includes handle members 306c and 306d that meet at split portion 306e. The split portion 306e is aligned with the weakened sections of the sheath section 306a. The introducer may also be referred to as an introducer cannula. The introducer 306 includes an inner lumen that extends longitudinally from an opening at the handle section 306b, through the handle section 306b and sheath section 306a, to an opening at the end of the sheath section 306a. Needle stylet 302 generally fits in the inner lumen of the introducer 306 and can be inserted into and withdrawn therefrom. The needle stylet 302 is generally tubular and includes a proximal end 302a and a distal end 302b. A needle stylet general includes a beveled edge to cut the tissue and an inner lumen allowing for a pliable pathway for a wireless neural stimulator device 308 to be tunneled down the inner lumen. The proximal end of the needle stylet 302 includes a stop portion 302c and the distal end 302b includes a beveled portion 302d to facilitate movement of the introducer 306 and stylet 302 through the layer of the tissue. The beveled portion 302d includes an opening. Needle stylet 302 also has its own inner lumen that extends from an opening at the proximal end 302a to the opening of the beveled portion 302d at the distal end 302b. As shown, the needle stylet 302 can be placed into and advanced through the inner lumen of the introducer 306 until the stop portion 302c engages the handle section 306b and the beveled portion 302d extends beyond the sheath section 306a. In this configuration, the introducer 306, along with the needle stylet 302 are inserted subcutaneously through surgical incision 301 or percutaneous opening and advanced laterally over the left chest cavity until the introducer 306 and needle stylet 302 are firmly placed within the tissue and the distal mouth of the introducer is medial of the intended stimulation site for implantation.

Figure 3B:
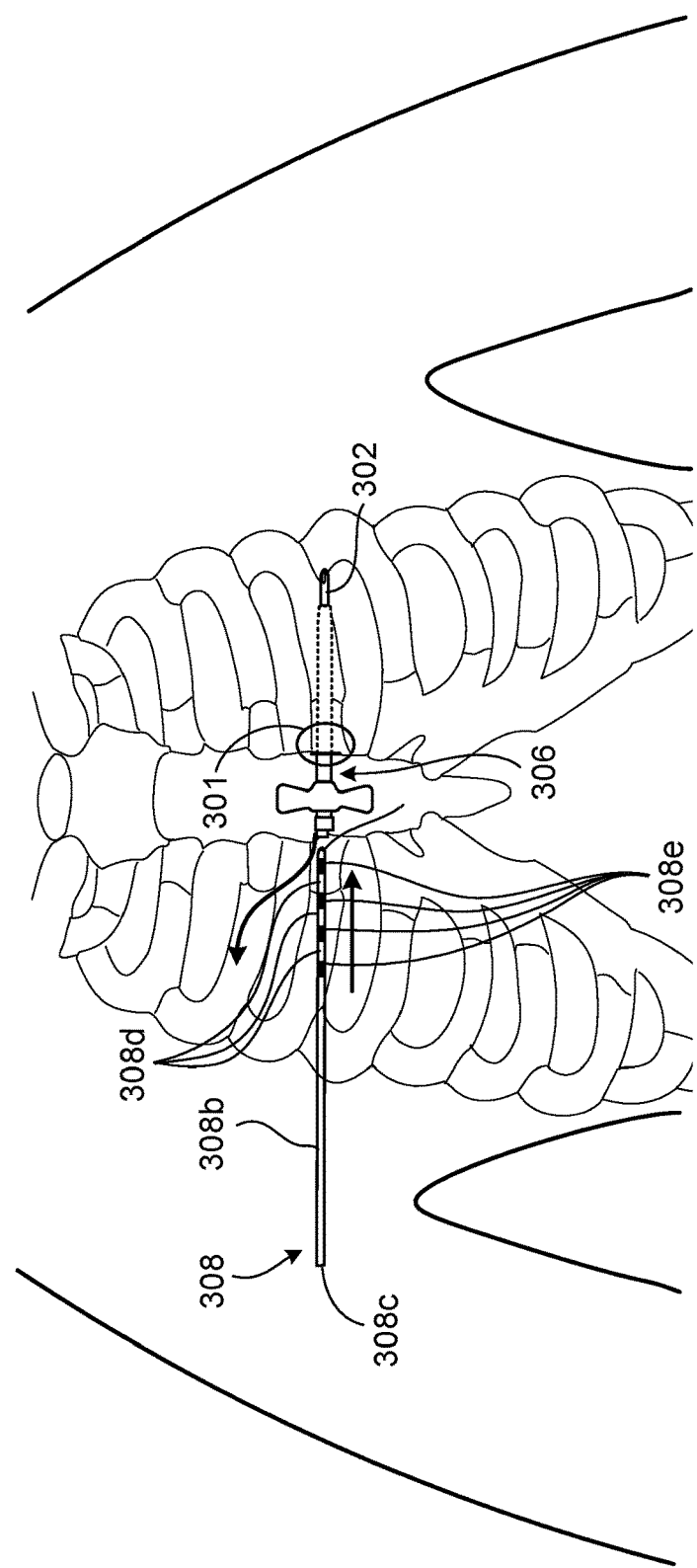

Referring to FIG. 3B, once the introducer 306 and needle stylet 302 are situated within the targeted tissue medium, the needle stylet 302 is removed, and a wireless neural stimulator device 308 is inserted through the opening, located at the proximal end of introducer 306, to the inner lumen of the introducer and advanced through the inner lumen until the tip 308a of the wireless neural stimulator device 308 passes through the opening of the beveled portion 302d into the subcutaneous parasternal space of the patient's left chest. For example, the physician may advance the wireless neural stimulator device 308 through the inner lumen until substantial resistance is met as a result of the tip 308a passing through the opening of the beveled portion 302d and contacting tissue. The physician may validate the correct placement of the wireless neural stimulator device by activating the wireless neural stimulator device with an external microwave field stimulator to induce stimulation of neural tissue at the stimulation site. When the patient is satisfied with the coverage, for example, when the patient expresses satisfaction with paresthesia resulting from the stimulation, the physician can proceed to stitch or steri-strip the needle entry site. Generally, all electrodes exit the inner lumen of introducer 306. In the event that strong resistance prevents the treating physician from advancing all electrodes out of the inner lumen, the electrodes can be tested after the introducer 306 is also removed. Leveraging feedback from the patient, the treating physician may not rely on imaging guidance when adjusting placement of the wireless neural stimulator device 308. In some instances, the physician may use a finger to sense the tip of the wireless neural stimulator device 308 as it exits the opening of the beveled portion 302. For context, the wireless neural stimulator device 308 is shaped and sized with the form factor to fit in the inner lumen of introducer 306. A portion of an example of the wireless neural stimulator device 308 is shown and described below in FIG. 3F. Inserting wireless neural stimulator device 308 into the parasternal space may not require fluoroscopic guidance while the insertion of a wireless neural stimulator device into an epidural space may involve monitoring the insertion by, for example, X-ray fluoroscopy. This difference is partly due to the difference in implantation depth.

Figure 3C:
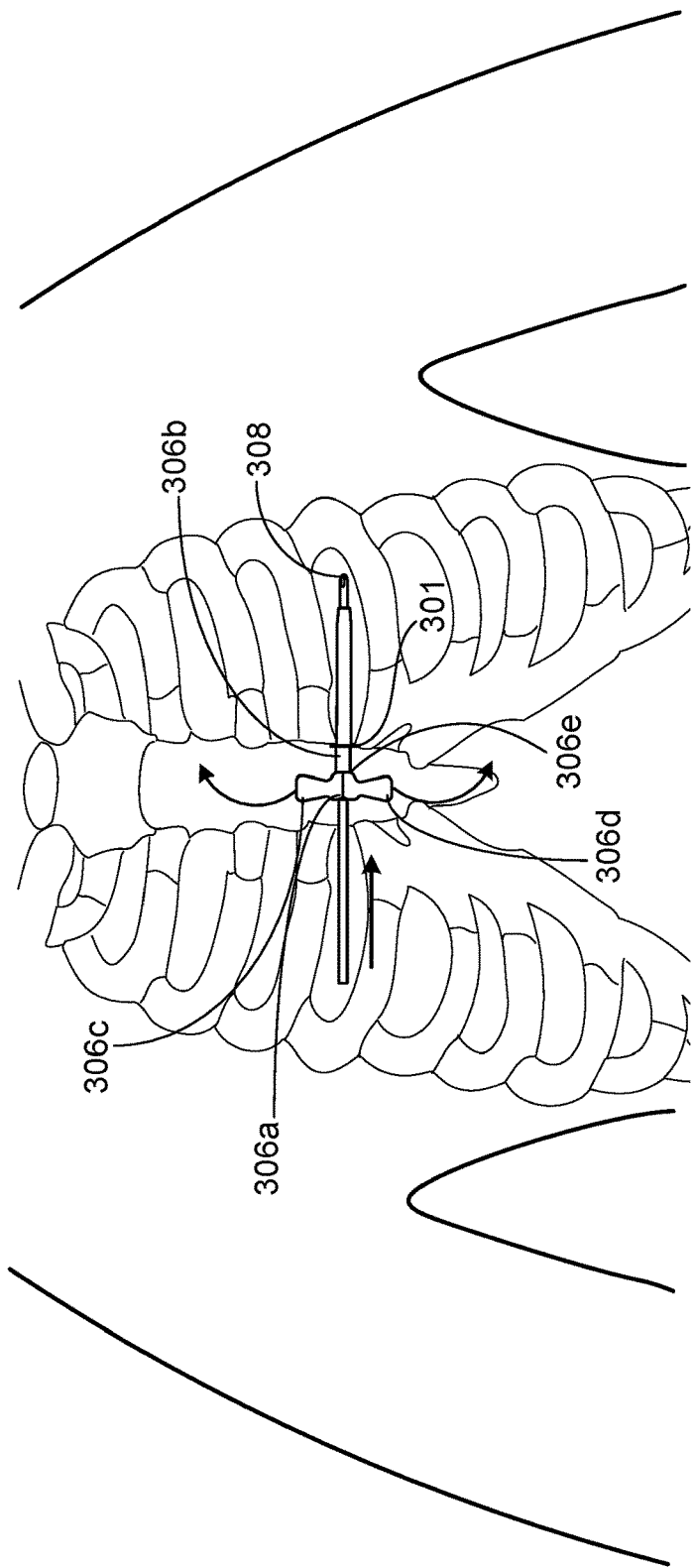

Thereafter, as illustrated in FIG. 3C, the needle stylet 302 is withdrawn when an physician pulls on the stop portion 302c to drag the needle stylet 302 through the inner lumen of the introducer 306, over the wireless neural stimulator device 308, and out of the opening of the inner lumen of the introducer 306 located at the handle section 306b. Next, the introducer 306 is withdrawn. In this example, handle members 306c and 306d of introducer are pulled apart as illustrated by the arrows, which results in the split portion 306e splitting apart. The physician continues pulling apart the handle members 306c and 306d, thereby splitting the sheath section 306a along the weakened sections, while also pulling the handles members 306c and 306d laterally away from the incision 301, which results in the sheath portion 306e being pulled out of the incision 301 so that only the device 308 remains.

Figure 3D:
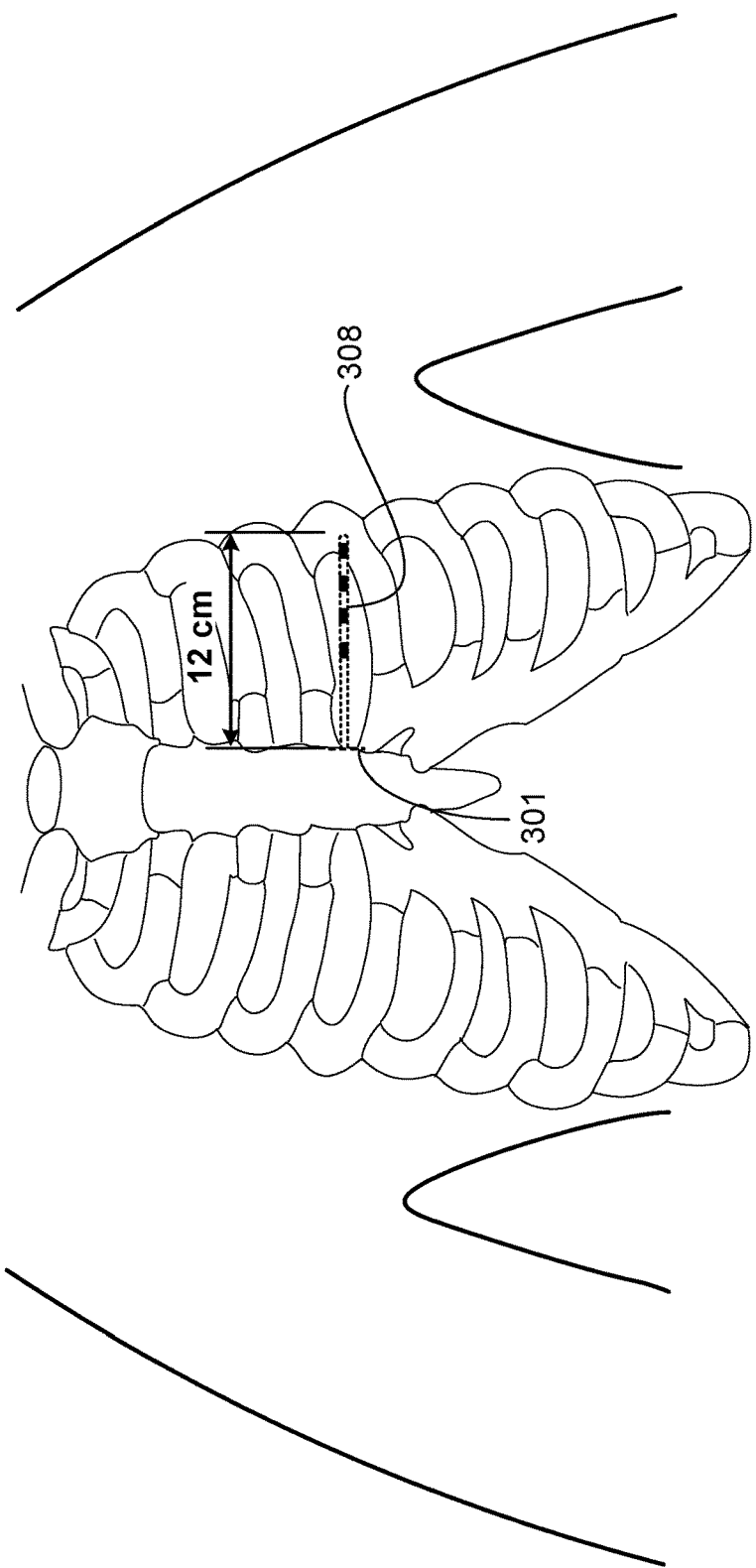

Referring to FIG. 3D, after the introducer 306 and stylet 302 have been removed, wireless neural stimulator device 308 may be anchored, for example, by suturing to the fascia or layer of "tougher" tissue below the skin, any excess portion of the device 308 extending outside of incision 301 may be trimmed, and the surgical incision 301 or percutaneous opening may be sealed. In some instances, the proximal end of wireless neural stimulator device 308 may be anchored to the surrounding tissue near the original site of surgical incision 301. In some instances, the anchoring may be accomplished by the physician running the suture stitch directly through the soft plastic body of the wireless neural stimulator device or loop suture around the wireless neural stimulator device 308 itself noninvasively. As illustrated, the distal end (or the tip) of wireless neural stimulator device 308 may be 25 cm or less away from the site of surgical incision 301 or percutaneous opening.

Figure 3E:
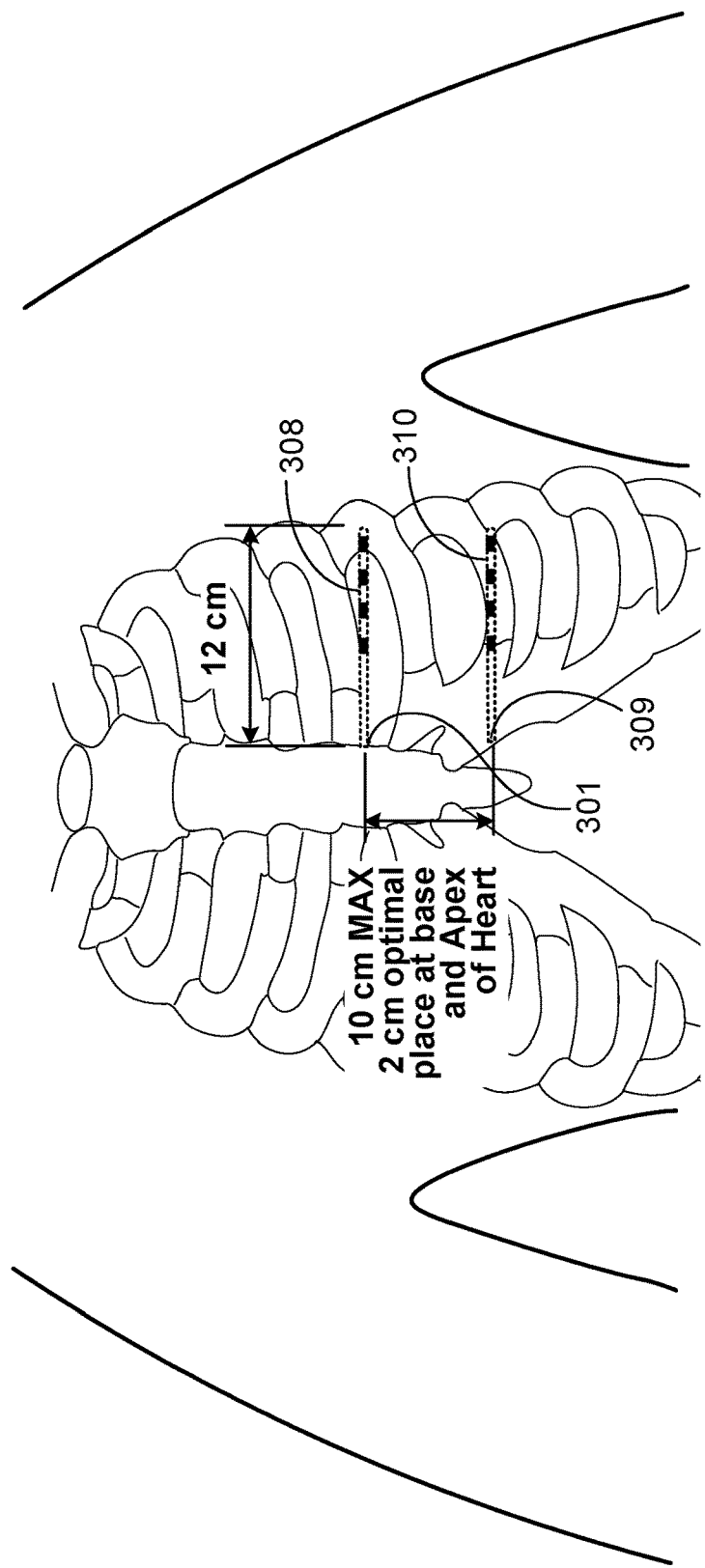

Multiple wireless neural stimulator devices may be implanted subcutaneously to treat angina because subcutaneous implantation tends to be less invasive and generally does not involve serious complications. In some instances, for example, when the pain relief being sought is diffuse rather than focused, implantation of multiple wireless neural stimulator devices may be warranted. This approach may render multiple implantations easier to perform. As illustrated in FIG. 3E, wireless neural stimulator devices 308 and 310 are implanted through surgical incisions 301 and 309, respectively, as described above in association with FIGS. 3A to 3D. In this example of treating angina pain, the separation of wireless neural stimulator devices 308 and 310 is typically no more than 10 cm. For example, both wireless neural stimulator devices 308 and 310 may be spaced 2 cm apart. In some instances, multiple wireless neural stimulator devices may be implanted through one surgical incision or percutaneous opening. To deliver efficient relief to the nerves that align along the same pathway of those associated with angina, wireless neural stimulator devices 308 and 310 may be at the parasternal space at the level of the base of the heart and apex of the heart.

Figure 3F:
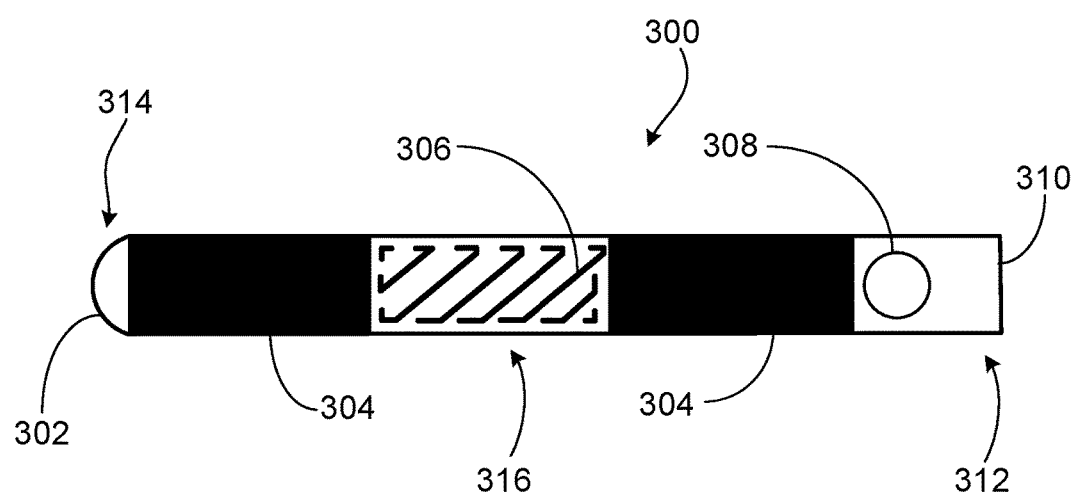
FIG. 3F illustrates a portion of an example of the wireless neural stimulator device.

FIG. 3F shows an example of a distal portion of a wireless neural stimulator device 308 that includes a non-conductive distal end 308a, a lead body 308b. Distal end 308a may have a rounded tip 318 with a smooth finish to allow for navigating through tissue. Wireless neural stimulator device 308 may also include cylindrically shaped electrodes 306e spaced at, for example, between 0.25 mm and 6.0 mm. Wireless neural stimulator device 308 may also include a soft plastic body that houses electronic circuitry 306d. Wireless neural stimulator device 308 may be implemented as described above, for example, with respect to any of FIGS. 1-2.

Figure 4A:
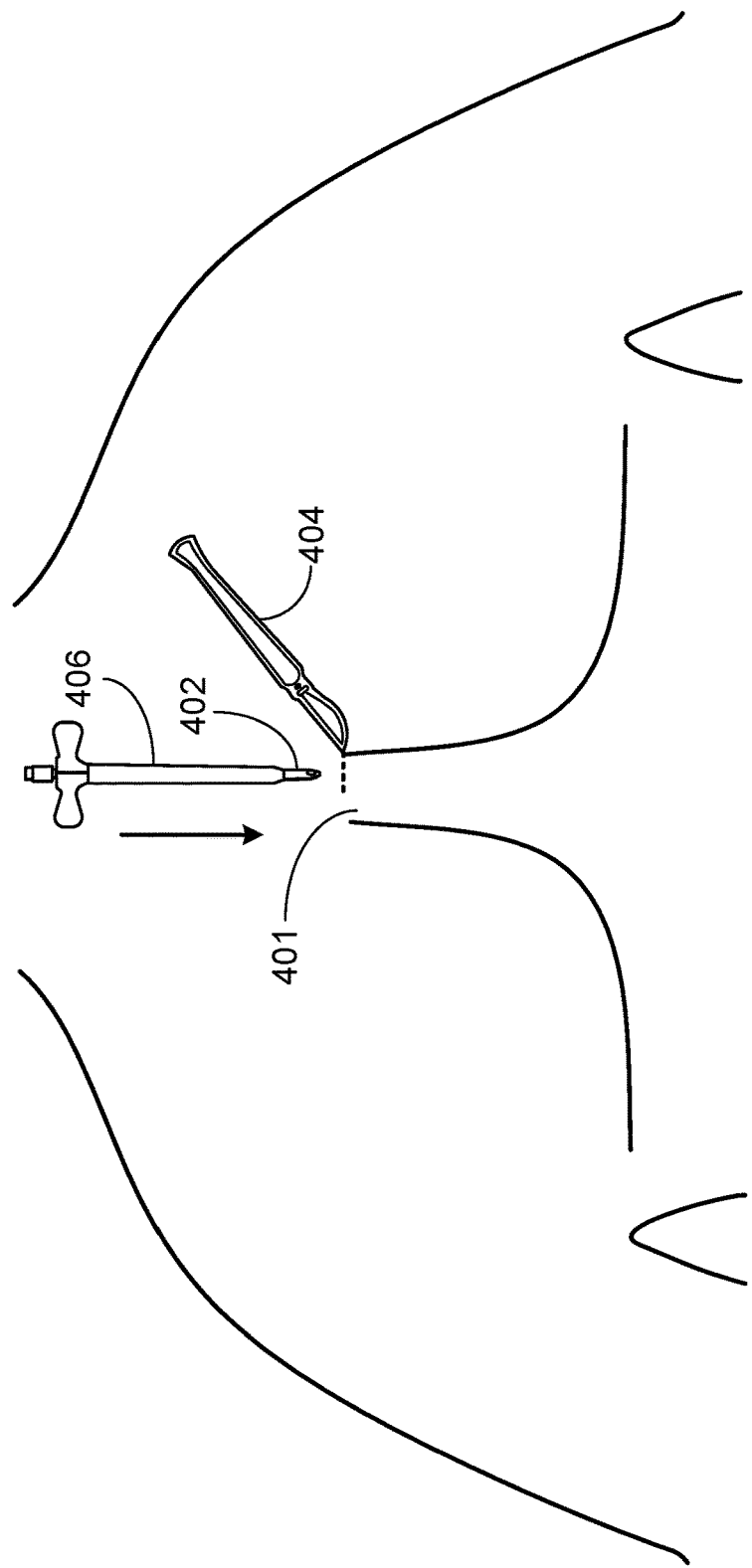
Figure 4C:
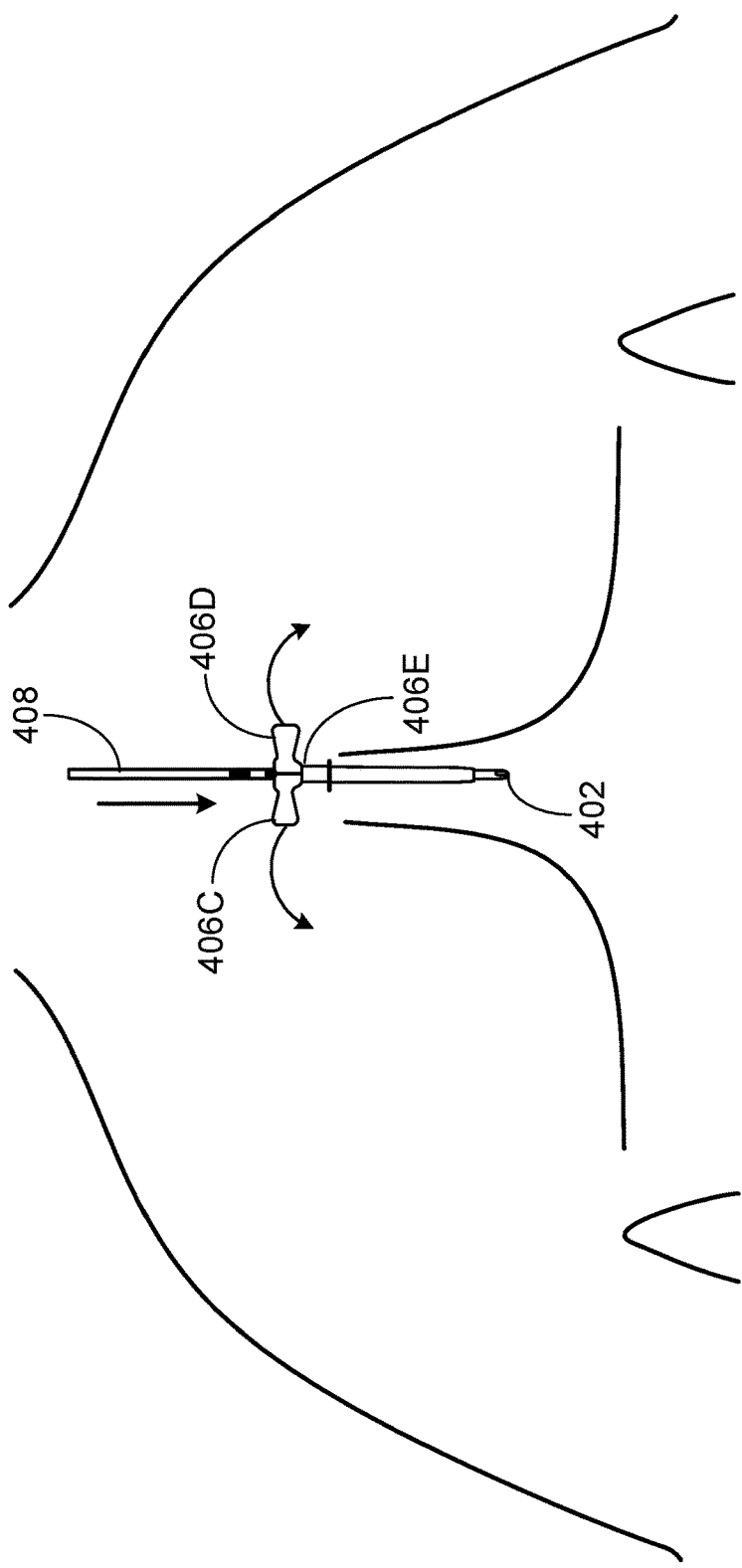

FIGS. 4A-4G illustrate an example of anterior implantation of wireless neural stimulator device outside the thoracic cavity. As illustrated in FIG. 4A, initially, a treating physician makes a surgical incision 401, for example, 2 mm long, on the anterior surface of the patient's thoracic cavity. As illustrated, the surgical incision is a transverse incision and near the midline on the patient's chest. The midline may also be known as the midplane. The incision point generally targets the parasternal space. In one example, surgical incision 401 may be made by cutting the skin using scalpel 404 and under local anesthesia, as explained above in association with FIG. 4A. Next, introducer 406, along with needle stylet 402, may be inserted through surgical incision 401 underneath the patient's skin and advanced in an inferior direction until the introducer 406 and needle stylet 402 are firmly placed within the tissue and the distal mouth of the introducer is anterior of the intended stimulation site for implantation. In some instances, the wireless neural stimulator device is advanced such that all electrodes exit the inner lumen and the introducer is removed. In other instances, the stimulator is only advanced until it contacts tissue and then the introducer is removed to expose the electrodes. General descriptions of introducer 406 and needle stylet 402 can be found above in discussions associated with FIG. 3A.

Referring to FIG. 4B, needle stylet 402 is removed and wireless neural stimulator device 408 is inserted through the proximal end of needle stylet 402, and into the parasternal space of the patient's chest, and advanced in an inferior direction, parallel to the midline of the parasternal space. Generally, the electrodes of wireless neural stimulator device 408 are expected to contact tissue beyond the opening of introducer sheath 402a. In one example, the physician may notice a sudden increase of resistance level indicating that the distal tip of wireless neural stimulator device 408 has exited the opening of introducer sheath 402a. The physician may then progress the device 408 forward until all electrodes are exposed to begin testing the implant site for appropriate therapeutic response. In some cases, if the treating physician experiences strong resistance such that the electrodes only partially exit the inner lumen, testing the electrodes may be deferred until after the introducer is removed. In another example, the physician may sense the placement of the wireless neural stimulator device 408 by using a finger and aligning the electrodes directly around sites of pain.

Thereafter, introducer 406 may be withdrawn from surgical incision 401. In this example, handle members 406*c* and 406*d* of introducer are pulled apart as illustrated by the arrows, which results in the split portion 406*e* splits apart. The physician continues pulling apart the handle members 406*c* and 406*d*, which splits the sheath section 406*a* along the weakened sections, while also pulling the handles members 406*c* and 406*d* laterally away from the incision 401. As a result, the sheath portion 306*e* being pulled out of the incision 401 so that only the wireless neural stimulator device 308 remains, similar to the motion described above in association with FIG. 3C, Handles 406A and 406B may also be known as tearaway handles. Subsequently, wireless neural stimulator device 308 may be anchored and surgical incision 401 may be sealed. In one example, the physician may run the suture stitch directly through the soft plastic body of the wireless neural stimulator device 308 or loop suture around the wireless neural stimulator device itself noninvasively, as discussed above in association with FIG. 3D.

Figure 4E:
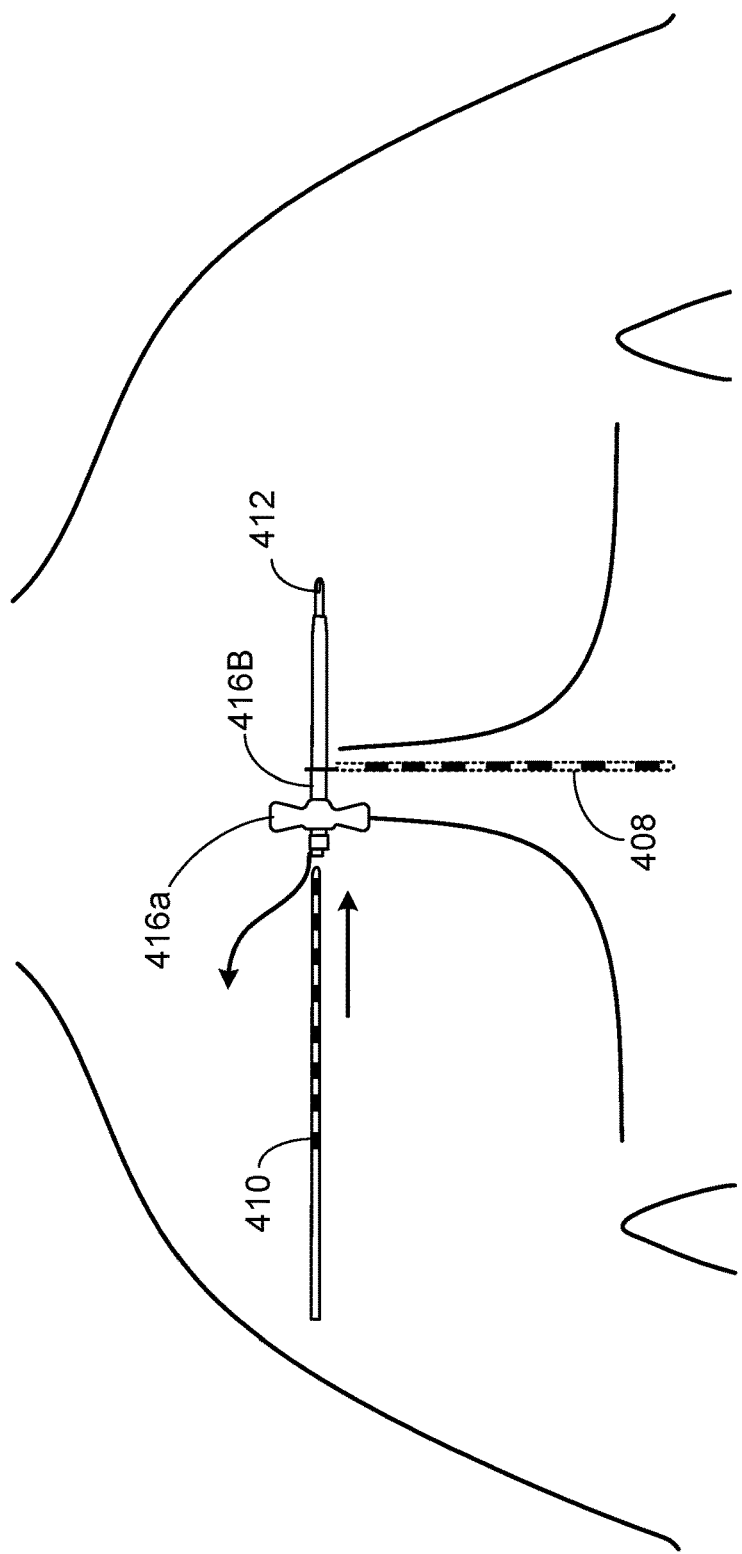

In FIG. 4D, while wireless neural stimulator device 408 has been implanted in the parasternal space along the midline of the patient's chest, another wireless neural stimulator device 410 may be implanted in the parasternal space on the level of the base of the heart and in the left chest of the patient. This implantation may use introducer 416 and needle stylet 412 in a manner similar to that described above in association with FIGS. 4A-4B. Yet, implanting wireless neural stimulator device 410 follows a horizontal insertion path, as illustrated in FIGS. 4E and 4F (and similarly illustrated and described in FIGS. 3A-3D).

Figure 4F:
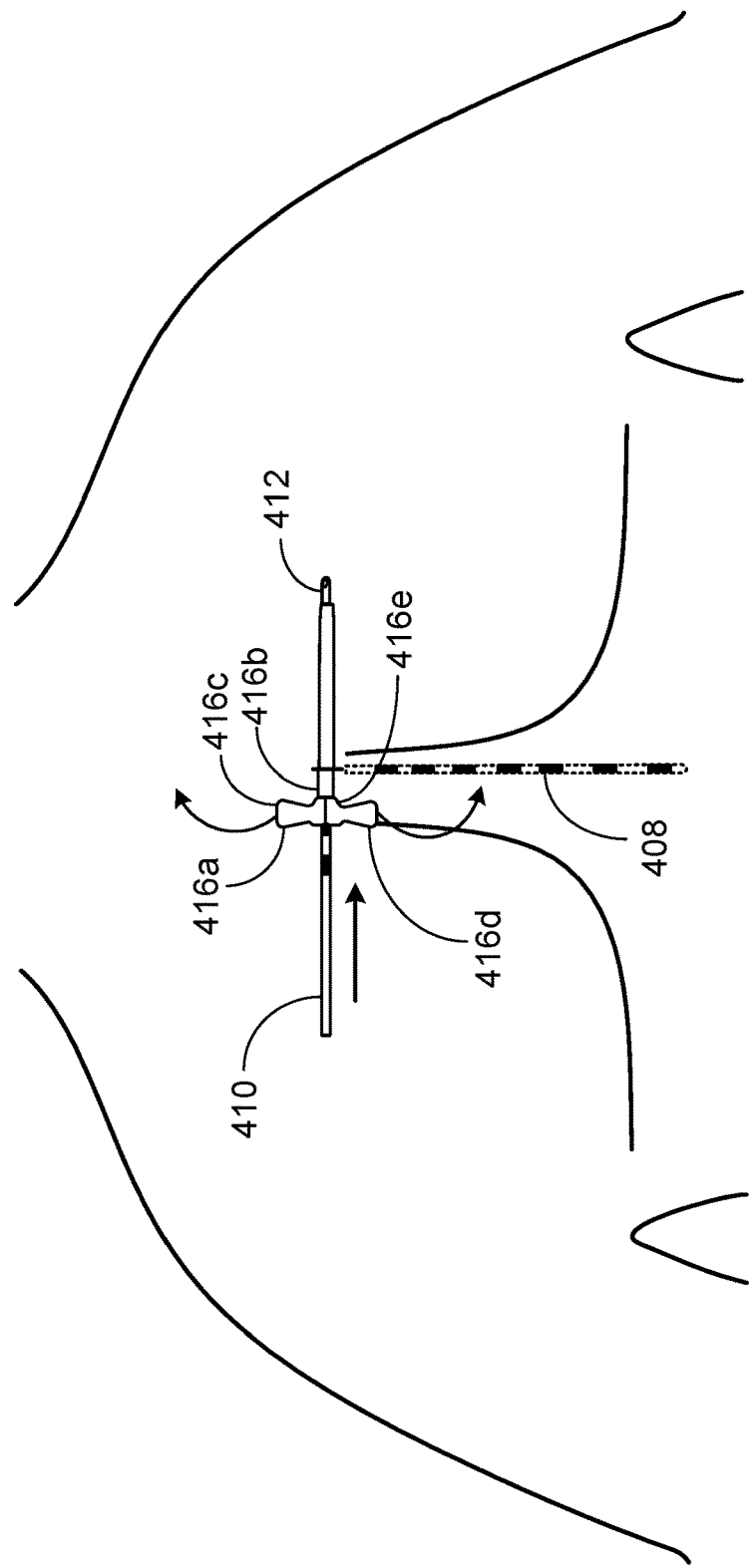

As illustrated in FIG. 4F, once wireless neural stimulator device 410 has been implanted, introducer 416 and needle stylet 412 may be withdrawn in a manner similar to that described above in association with FIG. 4C. Thereafter, wireless neural stimulator device 410 may be anchored or sutured to surrounding tissue in the parasternal space.

FIG. 4G illustrates wireless neural stimulator device 408 implanted vertically along the midline in the parasternal space with wireless neural stimulator device 410 implanted horizontally at the base of the heart and on the left side of the thoracic cavity. Wireless neural stimulator device 410 is implanted at a site that is lateral to wireless neural stimulator device 408.

Figure 5B:
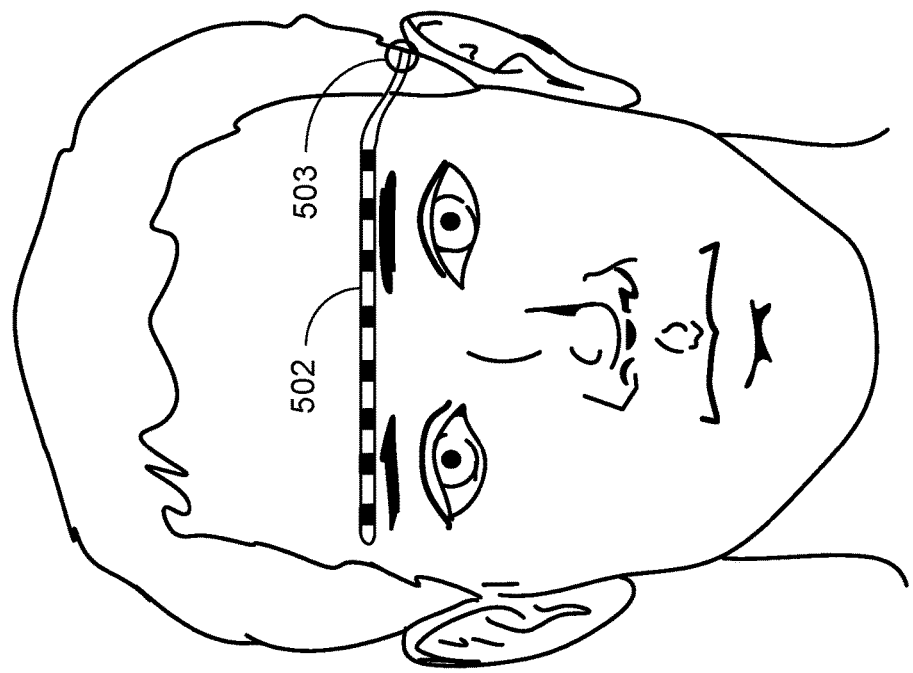
FIGS. 5A-5B illustrates an example of implanting a wireless neural stimulator device to treat craniofacial pain.
Figure 5A:
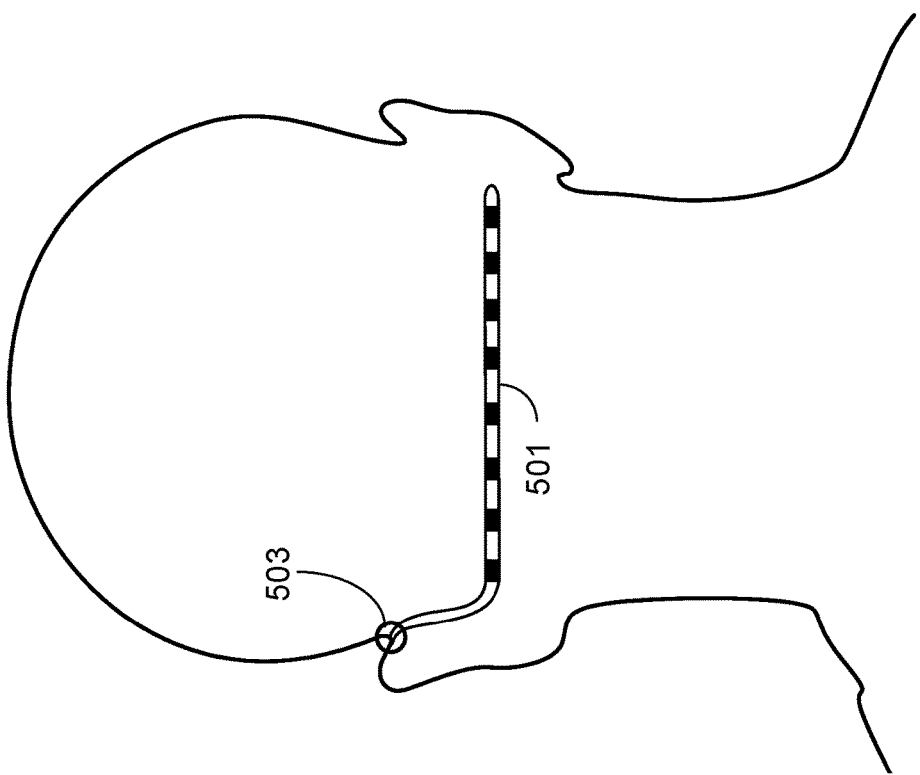

The above described implantation procedure is applicable to the treatment of other pains. FIGS. 5A-5B illustrates an example of implantation of wireless neural stimulator devices 501 and 502 to treat craniofacial pain and occipital pain. In particular, implantation of wireless neural stimulator devices 501 and 502 can utilize a common incision port, for example, entry point 503 above the left ear lobe. As illustrated below, wireless neural stimulator devices 501 and 502 can be implanted one at a time using the same assembly of introducer and needle style through entry point 503.

FIG. 5A depicts lateral subcutaneous placement of a wireless neural stimulator device 501 across the posterior cranium above the occipital crest to target the occipital nerve bundles, using entry point 503 above the left ear lobe. In this example, a treating physician makes a surgical incision (for example, less than 2 mm) at entry point 503 above the left ear of the patient. The incision point generally avoids the facial area to avoid leaving observable scar marks. In one example, surgical incision may be made by using a scalpel and under local anesthesia, as explained above in association with FIG. 4A. Next, a combination of an introducer and a needle stylet may be inserted through surgical incision underneath the patient's skin and in a downward motion. Thereafter, wireless neural stimulator device may be inserted through the proximal end of needle stylet. When the wireless neural device 308 reaches the level just above the occipital crest, an internal stylet with a bend may be utilized by the treating physician to lead the wireless neural stimulator device to turn in the subcutaneous space and then to follow a horizontal path in the direction of the right ear. As illustrated, the wireless neural stimulator device is advanced into the space of posterior cranium. Once the wireless neural stimulator device has been implanted to target the occipital nerve bundles, introducer and needle stylet can be withdrawn from surgical incision, for example, by using tear-away handles as discussed above in association with FIG. 4C. Subsequently, wireless neural stimulator device 501 may be anchored. In this example, entry point 503 is not sealed.

FIG. 5B depicts lateral placement of wireless neural stimulator across the supraorbital aspect to target the supra-orbital trigeminal nerve branch using the same entry point 503 above the left ear. In this example, a treating physician can insert a combination of an introducer and a needle stylet through the same entry point 503 underneath the patient's skin and in a horizontal manner and in the direction of the forehead. Thereafter, wireless neural stimulator device may be inserted through the proximal end of needle stylet and into the space of anterior cranium above the eyebrows. Once the wireless neural stimulator device has been implanted to target the supraorbital trigeminal nerve branch, introducer and needle stylet can be withdrawn from entry point 503, wireless neural stimulator device 502 may be anchored and surgical incision at entry point 503 may be sealed. Thereafter, an ear piece microwave field stimulator (MFS) can be mounted above the left ear to power wireless neural stimulator devices 501 and 502 with a single antenna to radiate electromagnetic energy to both wireless neural stimulator devices.

A number of implementations have been described. Nevertheless, it will be understood that various modifications may be made. Accordingly, other implementations are within the scope of the following claims.

What is claimed is:

1. A method for implanting a wireless neural stimulator device, the method comprising:
    forming an opening in a skin layer of a patient;
    inserting an assembly comprising an introducer and a needle stylet through the opening and underneath the skin layer to position the assembly adjacent a stimulation site on a tissue of the patient, the needle stylet mounted in an inner lumen of the introducer;
    withdrawing the needle stylet from the inner lumen of the introducer after positioning the assembly adjacent the stimulation site;
    inserting the wireless neural stimulator device through the inner lumen of the introducer and into the tissue to implant the wireless neural stimulator device at the stimulation site;
    pulling the introducer away from the wireless neural stimulator device in a manner that mechanically alters the introducer; and
    withdrawing the introducer in a mechanically altered state from the patient through the opening in a manner such that the wireless neural stimulator device remains positioned at the stimulation site.

2. The method of claim 1, wherein the introducer is of gauge 13 or smaller.

3. The method of claim 1, wherein inserting the assembly comprises inserting the assembly under ultrasound guidance.

4. The method of claim 1, wherein inserting the assembly comprises inserting the assembly under X-ray fluoroscopy.

5. The method of claim 1, further comprising validating placement of the wireless neural stimulator device by activating the wireless neural stimulator device using an external microwave field stimulator to induce neural stimulation at the stimulation site.

6. The method of claim 1, wherein the wireless neural stimulator device is implanted in the patient without implanting an implantable pulse generator (IPG) in the patient.

7. The method of claim 1, wherein the wireless neural stimulator device is implanted in the patient without connecting the wireless neural stimulator device to an external power source via a wire.

8. The method of claim 1, wherein the opening is a paramedian incision on an anterior surface of a thoracic cavity of the patient; and wherein the method further comprises, after inserting the assembly through the paramedian incision, advancing the assembly laterally until a distal mouth of the introducer is medial of the stimulation site.

9. The method of claim 1, wherein the opening is a transverse incision on an anterior surface of a thoracic cavity of the patient; and wherein the method further comprises, after inserting the assembly through the opening, advancing the assembly inferiorly until a distal mouth of the introducer is anterior of the stimulation site.

10. The method of claim 1, further comprising forming the opening above an ear of the patient.

11. The method of claim 10, further comprising:
after inserting the assembly through the opening, advancing the wireless neural stimulator device to a position above an occipital crest of the patient; and
subsequently bending the wireless neural stimulator device to position the wireless neural stimulator device in a posterior cranium space of the patient.

12. The method of claim 10, further comprising, after inserting the assembly through the opening, advancing the wireless neural stimulator device into an anterior cranium above eyebrows of the patient.

13. The method of claim 1, further comprising anchoring the wireless neural stimulator device to surrounding tissue at the stimulation site.

14. The method of claim 13, wherein anchoring the wireless neural stimulator device comprises suturing the wireless neural stimulator device to the surrounding tissue.

15. The method of claim 1, wherein the wireless neural stimulator device is implanted such that a distal end of the wireless neural stimulator device is located 12 cm or more from the opening in the skin layer.

16. The method of claim 1, further comprising implanting one or more additional wireless neural stimulator devices in the patient through one or both of the opening formed in the skin layer and one or more additional openings formed in the skin layer.

17. The method of claim 1, wherein the opening comprises a surgical incision or a percutaneous opening.

18. The method of claim 1, further comprising tearing the introducer.

19. The method of claim 18, further comprising splitting the introducer along a tear.

20. The method of claim 19, wherein the introducer comprises opposing proximal elements by which the introducer can be pulled apart along the tear.

21. The method of claim 20, further comprising pulling the introducer apart along a first direction that is substantially perpendicular to a second direction in which the introducer is withdrawn from the patient through the opening.

22. The method of claim 1, further comprising securing a proximal end of the wireless neural stimulator device to the patient at a location adjacent the opening in the skin layer.

23. The method of claim 1, wherein the wireless neural stimulator device is formed as an elongate member that houses electronic circuitry configured to wirelessly communicate with an IPG disposed external to the patient.

24. The method of claim 23, wherein the wireless neural stimulator device is configured to communicate with the IPG via electrical radiative coupling.

* * * * *